(12) United States Patent
Dietrich

(10) Patent No.: US 6,575,040 B2
(45) Date of Patent: Jun. 10, 2003

(54) ASPIRATION DEVICE INCLUDING PRESSURE MEASURING SYSTEM

(75) Inventor: Andreas Dietrich, Rebstein (CH)

(73) Assignee: Oertli-Instrumente AG, Berneck (CH)

( * ) Notice: Subject to any disclaimer, the term of this patent is extended or adjusted under 35 U.S.C. 154(b) by 0 days.

(21) Appl. No.: 10/131,180

(22) Filed: Apr. 25, 2002

(65) Prior Publication Data

US 2002/0157476 A1 Oct. 31, 2002

(30) Foreign Application Priority Data

Apr. 25, 2001 (CH) .............................................. 0756/01

(51) Int. Cl.[7] ................................................. G01L 7/00
(52) U.S. Cl. ...................................................... 73/756
(58) Field of Search ........................ 73/706, 715, 756, 73/730, 861.42, 861.43, 861.44

(56) References Cited

U.S. PATENT DOCUMENTS

| | | | | |
|---|---|---|---|---|
| 5,000,049 A | * | 3/1991 | Cooper et al. | 600/561 |
| 5,115,676 A | * | 5/1992 | Lee | 361/283.4 |
| 5,392,653 A | | 2/1995 | Zanger et al. | |
| 5,869,766 A | * | 2/1999 | Cucci et al. | 73/706 |
| 6,171,253 B1 | * | 1/2001 | Bullister et al. | 600/486 |

* cited by examiner

*Primary Examiner*—William L. Oen
(74) *Attorney, Agent, or Firm*—Browdy and Neimark

(57) ABSTRACT

A pressure measuring system has a line through which a fluid (4) flows, the line (3) having a central line section (5) in which, on a flattened outer side (6) of the line (3), a diaphragm is provided. The movements of the diaphragm, which are characteristic of pressure changes, are transmitted to a pressure sensor. In this case, the diaphragm is nondetachably connected to a protrusion (10) which points away from the line (3) and has an extension (12) which is oriented substantially transversely with respect to the longitudinal alignment of the line section (5) and, in a mechanical and simultaneously detachable way, acts on a force sensor as pressure sensor. A pressure measuring system is therefore provided which can be used for reconditioning in the autoclave sterilizer.

14 Claims, 3 Drawing Sheets

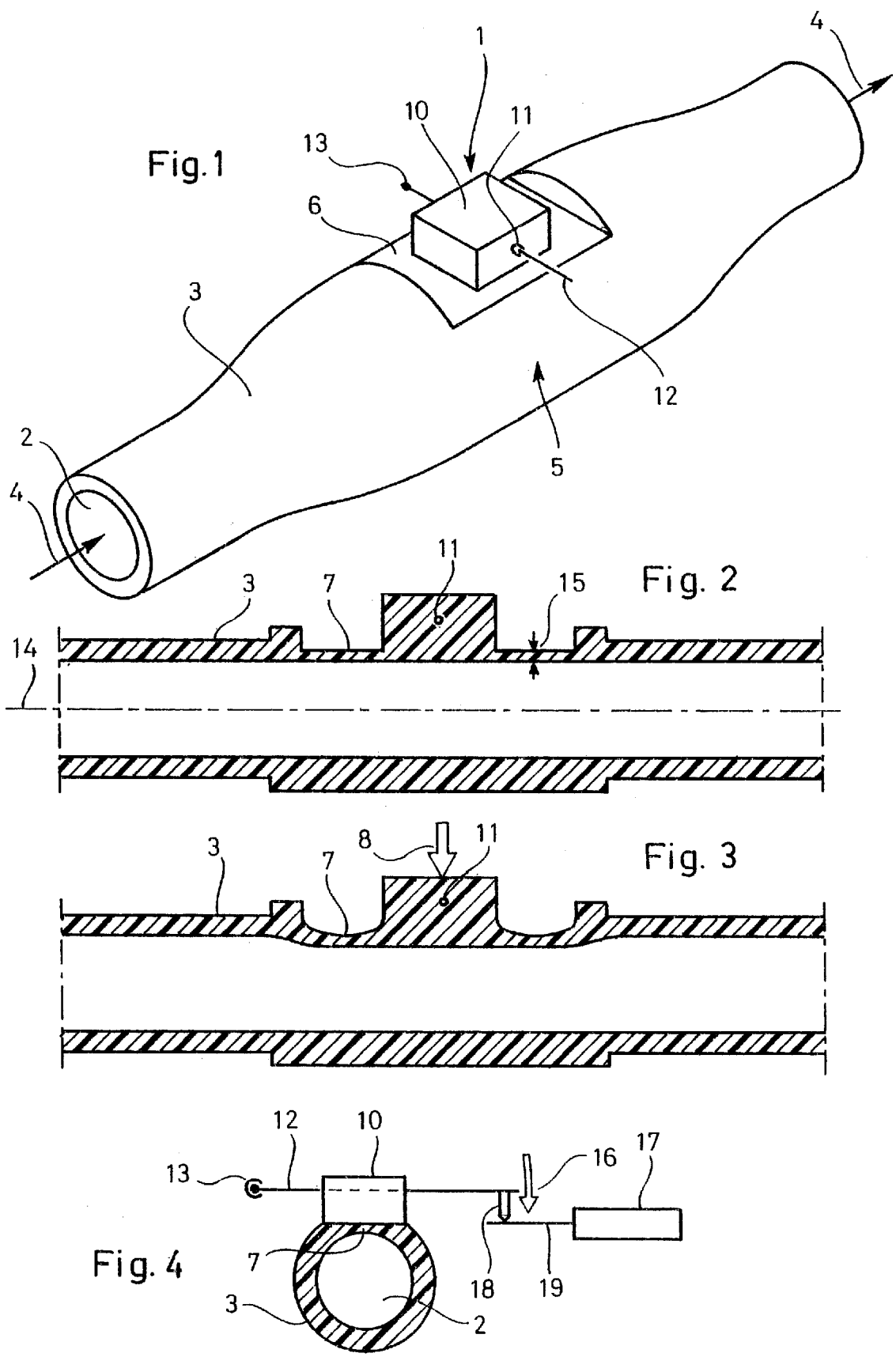

ASPIRATION DEVICE INCLUDING PRESSURE MEASURING SYSTEM

Figure 5:
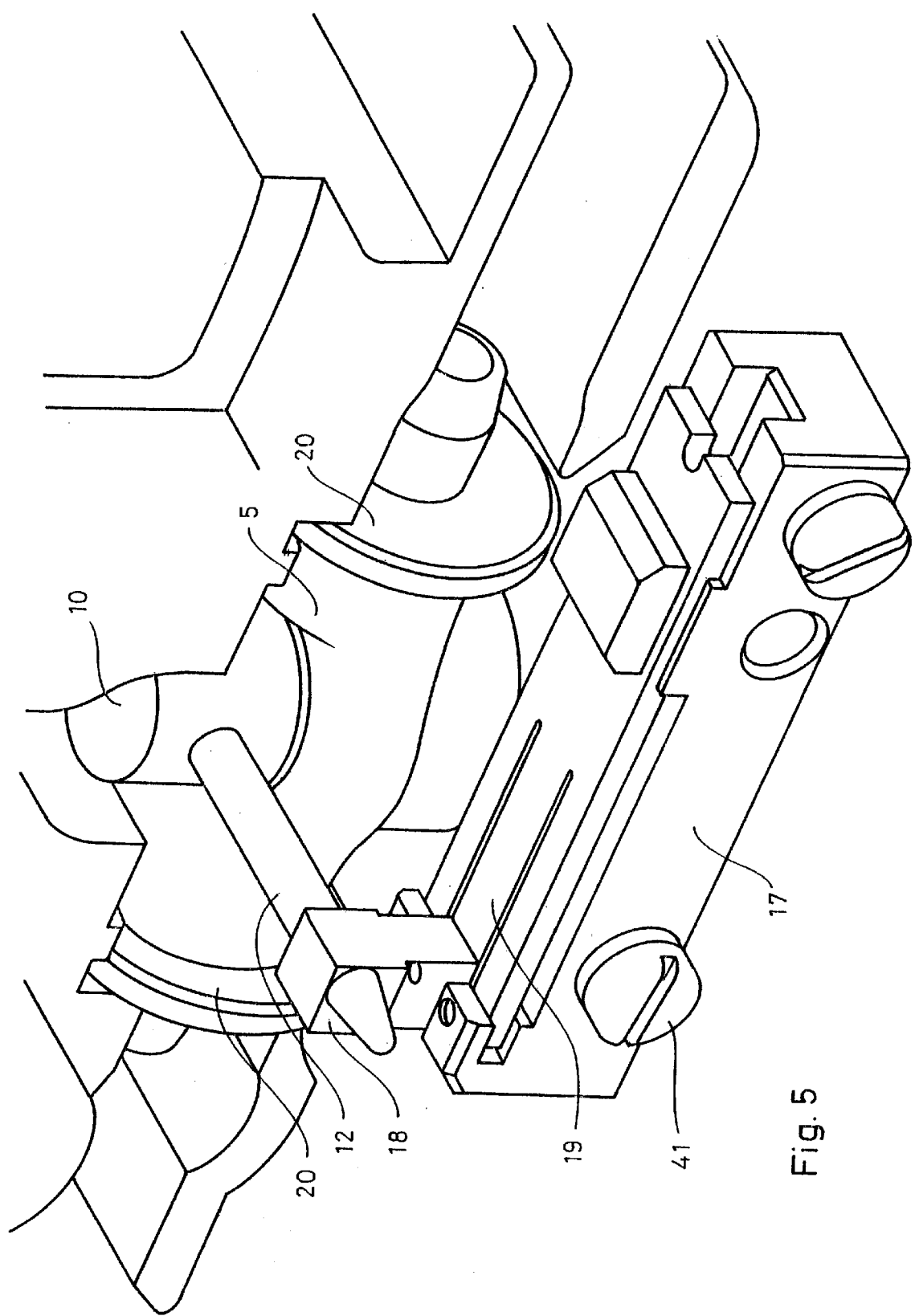

The invention relates to a pressure measuring system having a line through which a fluid flows, the line having a line section in which, on a flattened outer side of the line, there is provided a diaphragm whose movement, characteristic of pressure changes, can be transmitted to a pressure sensor.

Such a pressure measuring system is disclosed by U.S. Pat. No. 5,392,653. Such measuring systems are used in cartridges of an aspiration system. In an aspiration system, liquid is sucked up by means of a pump. The pump may be a roller pump or a Venturi pump, for example. Irrespective of the pump used, because of the resistance opposed to the flow in the tubes or lines in the event of an occlusion at the end of the tube, a vacuum will be produced in the tubes or lines. In conventional systems, the tube system is connected directly to a pressure sensor via a T branch.

Now, such aspiration systems are used, for example, in the cataract operation and are used to suck up the lens fragments produced during the operation, together with an infusion liquid. The current operation technique is to attract such lens parts by suction with the instrument connected to the aspiration system, to hold them firmly, bring them into a suitable position and break them down by means of ultrasound and subsequently suck them up. In the process, during a certain time, an occlusion is necessarily produced, since the suction opening is blocked by lens parts. After that, a greater vacuum builds up in the interior of the aspiration system. When the occlusion is loosened, which generally takes place very quickly, the vacuum is dissipated and, in the process, draws infusion liquid after it which, during the aforementioned operation, can lead to collapse of the anterior chamber of the eye to be operated on.

This after-suction and collapse effect is primarily high when there is air in the aspiration line. The volume assumed by the air under vacuum is reduced abruptly when the occlusion breaks and draws a particularly great amount of liquid after it. In the case of the known method with the use of a T branch, the inclusion of air is inevitable. In addition, in the case of this operating principle, the aspiration liquid can come into contact with the pressure sensor. Since this pressure sensor cannot be sterilized, there is the possibility of contamination of the patient with bacteria coming from the pressure sensor if the practitioner flushes back during the operation, which is necessary during certain operation steps.

With the device according to U.S. Pat. No. 5,392,653, the inclusion of air can be prevented and contact between the liquid in the tube system and a nonsterilizable sensor element is avoided. For this purpose, a metallic disk is fitted permanently to the pressure measuring chamber. This disk is coupled to a force or displacement sensor by means of magnetic force.

This system has the disadvantage that geometric conditions differing sharply from the circular cross section of the line system, that is to say the aspiration tube, prevail in the pressure measuring chamber. Because of this it is difficult to fill the chamber completely with fluid, and the lens fragments that are sucked up often remain stuck in the chamber. It is not possible to use this tube system for reconditioning in the autoclave sterilizer, since there is no possibility of emptying it completely and rinsing out the lens fragments reliably.

On the basis of this prior art, the invention is based on the object of specifying a pressure measuring system of the type mentioned at the beginning which can be used for reconditioning in the autoclave sterilizer.

This object is achieved, for a pressure measuring system of the type mentioned at the beginning, by a device according to the present invention.

The fact that the diaphragm is nondetachably connected to a protrusion which points away from the line and has an extension which is oriented substantially transversely with respect to the longitudinal alignment of the line section means that the cross section of the line system can be kept substantially circular, with the corresponding rinsing advantages.

The fact that this protrusion has a hole, through which the extension projects in the shape of a pin, means that a force sensor can have the excursions of the diaphragm applied to it in a simple way, mechanically and simultaneously detachably.

Further advantageous embodiments are identified in the subclaims.

Figure 6:
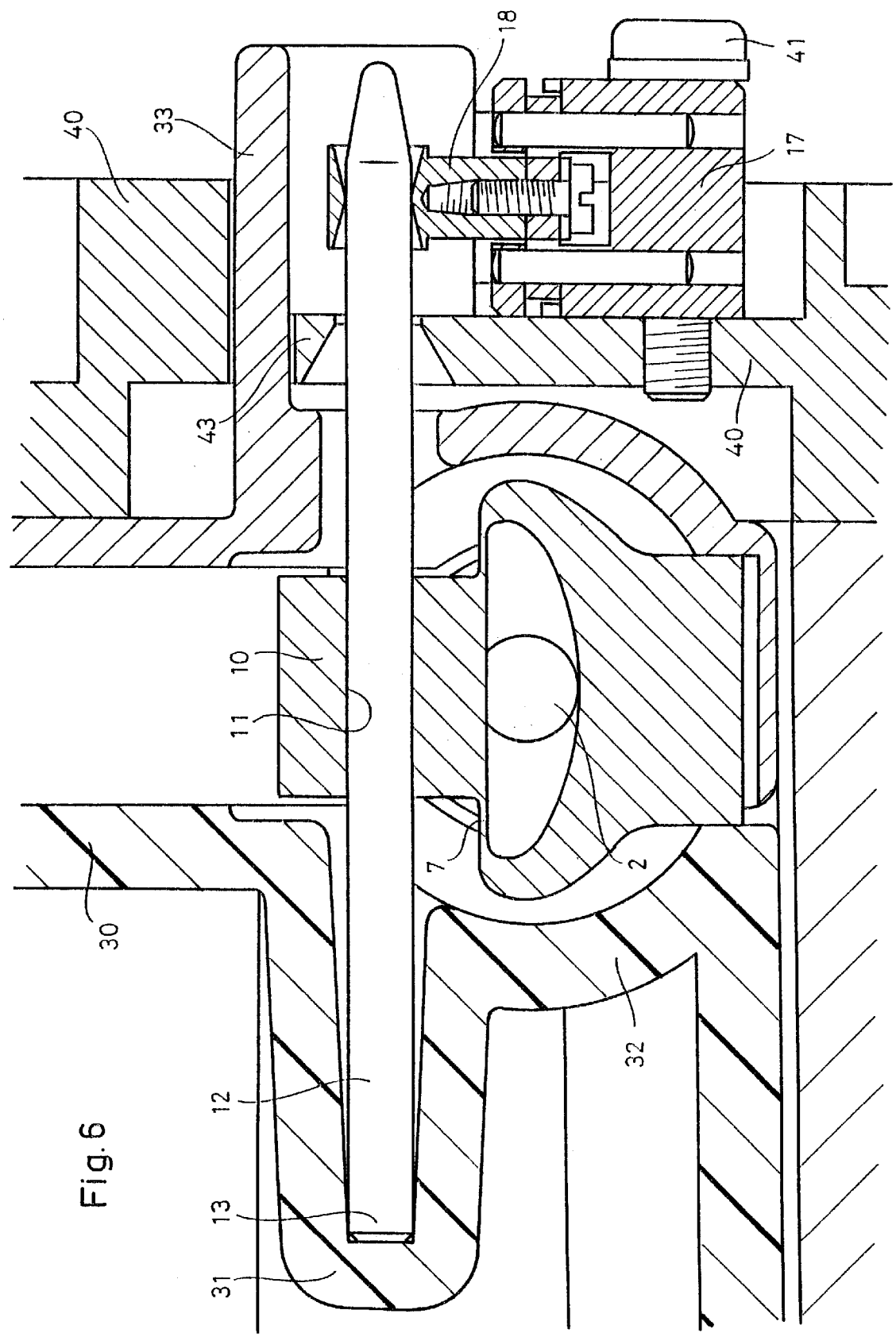

An exemplary embodiment of the invention will be described below by way of example and with reference to the appended drawings, in which:

FIG. 1 shows a perspective illustration of an arrangement according to the invention, FIG. 2 shows a sectional drawing through the arrangement of FIG. 1 under normal pressure conditions, FIG. 3 shows a sectional drawing through the arrangement of FIG. 1 under vacuum, FIG. 4 shows a cross-sectional view through the tube in the region of the rod, FIG. 5 shows an exemplary embodiment of a way of converting the diaphragm movement according to FIG. 4, and FIG. 6 shows a sectional view of the exemplary embodiment of FIG. 5.

In the exemplary embodiment according to the invention, it is an objective to perform the pressure measurement with a pressure measuring element 1 which continues the circular cross section 2 of the aspiration tube 3 as far as possible without change, and therefore eliminates the inclusion of air, does not keep lens fragments caught and, overall, can be rinsed satisfactorily.

FIG. 1 shows a perspective illustration of such an arrangement according to the invention. A fluid indicated by the arrows 4 flows through the aspiration tube 3. In the middle of FIG. 1, a line section 5 is illustrated in which, on a flattened outer side 6 of the line 3, a diaphragm 7 that can be seen in FIG. 2 is provided. The diaphragm 7 is nondetachably connected to a protrusion 10 which points away from the line 3 and which, in the exemplary embodiment illustrated in FIG. 1, has a hole 11, in which a pin 12 can be inserted. The pin 12 is attached to a fixed point 13, so that movements of the diaphragm 7 are converted by movements of the protrusion 10 into amplified pivoting movements of the pin 12.

FIG. 2 now shows a sectional drawing through the arrangement of FIG. 1 under normal pressure conditions. A piece of tube, the tube section 5, is provided with the thin-walled diaphragm 7 which, when a vacuum occurs in the tube 3, indicated by the arrow 8 in FIG. 3, moves in the direction of the center of the tube, which is defined by the longitudinal axis 14. FIG. 3 shows the sectional drawing through the arrangement of FIG. 1 under such a vacuum 8. The diaphragm 7 has a thickness 15 of 0.2 millimeters, for example. The deformations of this diaphragm 7 are illustrated exaggerated in FIG. 2 for the purpose of clarification.

FIG. 4 shows a schematic cross-sectional view through the tube 3 in the region of the pin 12. The pin 12 is anchored at its pivot 13 and can pivot only about the axis designated by the arrow 16. It is therefore possible to transmit a very small movement of the diaphragm 7 to a force sensor 17. Here, the pin 12 engages in a journal 18, which transmits the movement to an extension arm 19 of the force sensor 17.

FIG. 5 shows an exemplary embodiment of a pressure measuring system having such a conversion means according to FIG. 4. The tube section 5 ends in two flanges 20 to be connected to a line system. The pressure measuring chamber is illustrated in the contracted state. The protrusion 10 is cylindrical. The metallic pin 12, which is clamped in on one side at the point 13, hidden and not visible here, as a lever then transmits the movement of the diaphragm 7 to the force sensor 17.

FIG. 6 shows the exemplary embodiment of FIG. 5 in a sectional view. Here, the installation principle in particular becomes clear. The pressure measuring chamber in the tube section 5, the transmission pin 12 and the entire tube system are integrated in a cartridge 30 made of plastic. This cartridge 30 also includes the bearing 31 for the pin 12 and the encapsulation 32 of the pressure measuring chamber. On the other hand, the pressure sensor 17 is a constituent part of a cartridge holder 40 and is connected firmly to the latter via a screw connection 41. When the cartridge 30 is pushed into the cartridge holder 40, the coupling pin 12 is centered cleanly and connected to the pressure sensor 17 by means of the guide protrusion 33, which is a constituent part of the cartridge 30 and interacts with the guide element 43 belonging to the cartridge holder.

What is claimed is:

1. A pressure measuring system comprising
    a line (3) through which a fluid (4) flows, wherein the line (3) has a line section (5) which comprises a flattened outer side (6) of the line (3),
    a diaphragm (7) comprising said flattened outer side (6) of the line (3), whose movement, characteristic of pressure changes, can be transmitted to a force sensor (17),
    a protrusion (10) connected nondetachably to said diaphragm (7) and pointing away from the line (3),
    the system further comprising
        an extension (12) which is oriented substantially in a cross-sectional plane of the line perpendicular to the fluid flow and tangentially with respect to the radial direction of the line section (5) and being able to act, in a mechanical and simultaneously detachable way, on the force sensor (17).

2. The pressure measuring system as claimed in claim 1, wherein the extension (12) engages in a journal (18) which is arranged transversely with respect thereto and with which an extension arm (19) clamped in on one side and belonging to the force sensor (17) can be acted on.

3. The pressure measuring system as claimed in claim 1 or 2, wherein said protrusion (10) has a hole (11), through which the extension projects in the shape of a pin (12), which, by a mechanical contact (18, 19), makes contact in a detachable way with the force sensor (17).

4. The pressure measuring system as claimed in claim 3, wherein, on the side opposite the force sensor (17), the pin (12) is attached for rotational or pivotal movement at a point (13) that is fixed with respect to the line (3).

5. The pressure measuring system as claimed in claim 1,
    wherein the line section (5) with protrusion (10) and extension (12) is integrated in a cartridge (30),
    wherein the force sensor (17) is fixed in a cartridge holder (40), and
    wherein the cartridge (30) and the cartridge holder (40) have complementary guide elements (33, 43), so that when the cartridge (30) is inserted into the cartridge holder (40), the extension (12) can be connected in a centered manner to the force sensor (17).

6. The pressure measuring system as claimed in claim 5, wherein the guide element (43) of the cartridge holder (40) has a hole through which the extension (12) can be guided, so that it engages in a journal (18) belonging to the force sensor (17).

7. The pressure measuring system as claimed in claim 2,
    wherein the line section (5) with protrusion (10) and extension (12) is integrated in a cartridge (30),
    wherein the force sensor (17) is fixed in a cartridge holder (40), and
    wherein the cartridge (30) and the cartridge holder (40) have complementary guide elements (33, 43), so that when the cartridge (30) is inserted into the cartridge holder (40), the extension (12) can be connected in a centered manner to the force sensor (17).

8. The pressure measuring system as claimed in claim 7, wherein the guide element (43) of the cartridge holder (40) has a hole through which the extension (12) can be guided, so that it engages in a journal (18) belonging to the force sensor (17).

9. The pressure measuring system as claimed in claim 3,
    wherein the line section (5) with protrusion (10) and extension (12) is integrated in a cartridge (30),
    wherein the force sensor (17) is fixed in a cartridge holder (40), and
    wherein the cartridge (30) and the cartridge holder (40) have complementary guide elements (33, 43), so that when the cartridge (30) is inserted into the cartridge holder (40), the extension (12) can be connected in a centered manner to the force sensor (17).

10. The pressure measuring system as claimed in claim 9, wherein the guide element (43) of the cartridge holder (40) has a hole through which the extension (12) can be guided, so that it engages in a journal (18) belonging to the force sensor (17).

11. The pressure measuring system as claimed in claim 4,
    wherein the line section (5) with protrusion (10) and extension (12) is integrated in a cartridge (30),
    wherein the force sensor (17) is fixed in a cartridge holder (40), and
    wherein the cartridge (30) and the cartridge holder (40) have complementary guide elements (33, 43), so that when the cartridge (30) is inserted into the cartridge holder (40), the extension (12) can be connected in a centered manner to the force sensor (17).

12. The pressure measuring system as claimed in claim 11, wherein the guide element (43) of the cartridge 4, holder (40) has a hole through which the extension (12) can be guided, so that it engages in a journal (18) belonging to the force sensor (17).

13. A line (3) for use with a pressure measuring system comprising
    a diaphragm (7) being part of the line (3), whose movement (8), characteristic of pressure changes, can be transmitted to a force sensor (17),
    a protrusion (10) connected nondetachably to said diaphragm (7) and pointing away from the line (3),
    wherein the line (3) has a line section (5),
    wherein the line section (5) comprises a flattened outer side (6) of the line (3),
    wherein the diaphragm (7) is provided on said flattened outer side (6) of the line section (5) of the line (3), and wherein an extension (12) can be coupled with the protrusion in such a way, that it is orientable substantially in a cross-sectional plane of the line perpendicular to the fluid flow and tangentially with respect to the radial direction of the line section (5) and being able to act, in a mechanical and simultaneously detachable way, on the force sensor (17).

14. A pressure measuring system partially incorporated within an aspiration tube (3) of a cataract surgery instrument for sucking lens fragments produced during cataract surgery, a part of said pressure measuring system which is part of said aspiration tube (3) comprising a flattened portion (6) of a wall of said tube (3), said flattened portion (6) comprising a thinned portion (7) which functions as a sole diaphragm of said pressure measuring system, a protrusion (10) extending from said thinned portion (7) in a direction away from the axis of said tube, said pressure measuring system further comprising an elongated arm (12) extending from said protrusion (10) at an angle therefrom and movable with said thinned portion (7) acting as a diaphragm, said elongated element (12) having a first end portion which is fixed relative to movement of said thinned portion (7) acting as a diaphragm, and a second end portion on an opposite side of said protrusion (10) from said first end portion, said second end portion being movable with movement of said thinned portion (7) acting as a diaphragm, said second end portion of said elongated element (12) being operably associated with a force sensor (17), whereby said force sensor (17) is adapted to sense pressure variations within said aspiration tube (3) upon deflections of said thinned portion (7) of said tube acting as a diaphragm.

* * * * *